United States Patent [19]

Jang

[11] Patent Number: 4,958,634
[45] Date of Patent: Sep. 25, 1990

[54] LIMACON GEOMETRY BALLOON ANGIOPLASTY CATHETER SYSTEMS AND METHOD OF MAKING SAME

[76] Inventor: G. David Jang, 204 E. South St., Redlands, Calif. 92373

[21] Appl. No.: 47,049

[22] Filed: May 6, 1987

[51] Int. Cl.$^5$ .................................................. A61M 29/02
[52] U.S. Cl. ...................................... 606/194; 604/96; 604/101; 604/103
[58] Field of Search ................... 128/344, 348.1 D, 10, 128/207.15, 303.1, 303.11; 604/96–103, 21; 264/573

[56] References Cited

U.S. PATENT DOCUMENTS

| | | | |
|---|---|---|---|
| 1,690,995 | 11/1928 | Pratt | 128/344 |
| 2,799,273 | 7/1957 | Oddo | 128/325 |
| 3,045,677 | 7/1962 | Wallace | 128/349 |
| 3,211,152 | 10/1965 | Stern | 128/207.15 |
| 3,811,448 | 5/1974 | Morton | 604/102 |
| 4,040,413 | 8/1977 | Ohshiro | 604/101 X |
| 4,091,816 | 5/1978 | Elam | 128/351 |
| 4,183,102 | 1/1980 | Guiset | 128/344 X |
| 4,195,637 | 4/1980 | Gruntzig et al. | 128/348 |
| 4,295,464 | 10/1981 | Shihata | 128/1 |
| 4,327,736 | 5/1982 | Inoue | 128/349 |
| 4,338,942 | 7/1982 | Fogarty | 128/325 |
| 4,404,971 | 9/1983 | LeVeen et al. | 128/348 |
| 4,411,055 | 10/1983 | Simpson et al. | 264/573 X |
| 4,423,725 | 1/1984 | Baran et al. | 128/207 |
| 4,430,076 | 2/1984 | Harris | 604/96 |
| 4,445,892 | 5/1984 | Hussein et al. | 604/101 |
| 4,456,011 | 6/1984 | Warnecke | 128/325 |
| 4,490,421 | 12/1984 | Levy | 128/344 X |
| 4,520,823 | 6/1985 | LeVeen et al. | 128/348 |
| 4,527,549 | 7/1985 | Gabbay | 128/1 |
| 4,546,759 | 10/1985 | Solar | 128/1 D |
| 4,554,929 | 11/1985 | Samson et al. | 128/772 |
| 4,571,240 | 2/1986 | Samson et al. | 604/96 |
| 4,573,470 | 3/1986 | Samson et al. | 128/344 |
| 4,573,966 | 3/1986 | Weikl et al. | 604/53 |
| 4,576,142 | 3/1986 | Schiff . | |
| 4,581,017 | 4/1986 | Sahota | 604/101 |
| 4,638,805 | 1/1987 | Powell | 128/344 |
| 4,641,654 | 2/1987 | Samson et al. | 128/344 |
| 4,655,746 | 4/1987 | Daniels et al. | 604/53 |
| 4,697,573 | 10/1987 | Schiff | 128/1 D |
| 4,744,366 | 5/1988 | Jang | 128/344 |
| 4,763,654 | 8/1988 | Jang | 128/344 |
| 4,777,951 | 10/1988 | Cribier et al. | 128/344 |

FOREIGN PATENT DOCUMENTS

| | | | |
|---|---|---|---|
| 2328482 | 5/1977 | France . | |
| 0654214 | 2/1986 | Switzerland | 604/101 |

OTHER PUBLICATIONS

*Angioplasty*, G. David Jang (1986) (previously submitted).

Primary Examiner—Dalton L. Truluck
Assistant Examiner—Denise W. DeFranco
Attorney, Agent, or Firm—Knobb, Marten, Olson & Bear

[57] ABSTRACT

Disclosed in an angioplasty catheter comprising a catheter shaft having a distal end and at least one, and preferably two, angioplasty balloons on the distal end of the catheter shaft, wherein the distal end of the catheter and the balloons are formed from a single monolithic piece of polymer material. The distal end of the catheter may also include additional balloons formed from the same piece of polymer material. Each of the balloons is separately inflatable and deflatable by virtue of a separate lumen running through the catheter shaft to the balloon. Also disclosed is a method for making angioplasty balloons as described above, comprising the steps of forming from a single piece of polymer material the length of catheter shaft material having at least a first lumen therein, wherein each lumen has an outer wall and, if there are more than one lumen, each lumen has a common wall where the outer walls of at least two lumens converge, sealing the distal end of the first lumen to form a first sealed lumen, applying pressure to the proximal end of the first sealed lumen and heating the outer wall thereof to expand the outer wall of the first sealed lumen inside of first die to form a first balloon therefrom having dimensions determined by the dimensions of the interior of the die. Additional balloons may be formed on the catheter in the same manner.

25 Claims, 4 Drawing Sheets

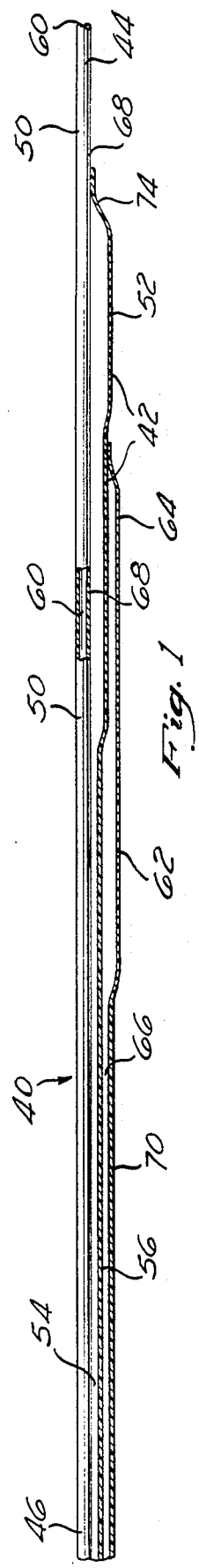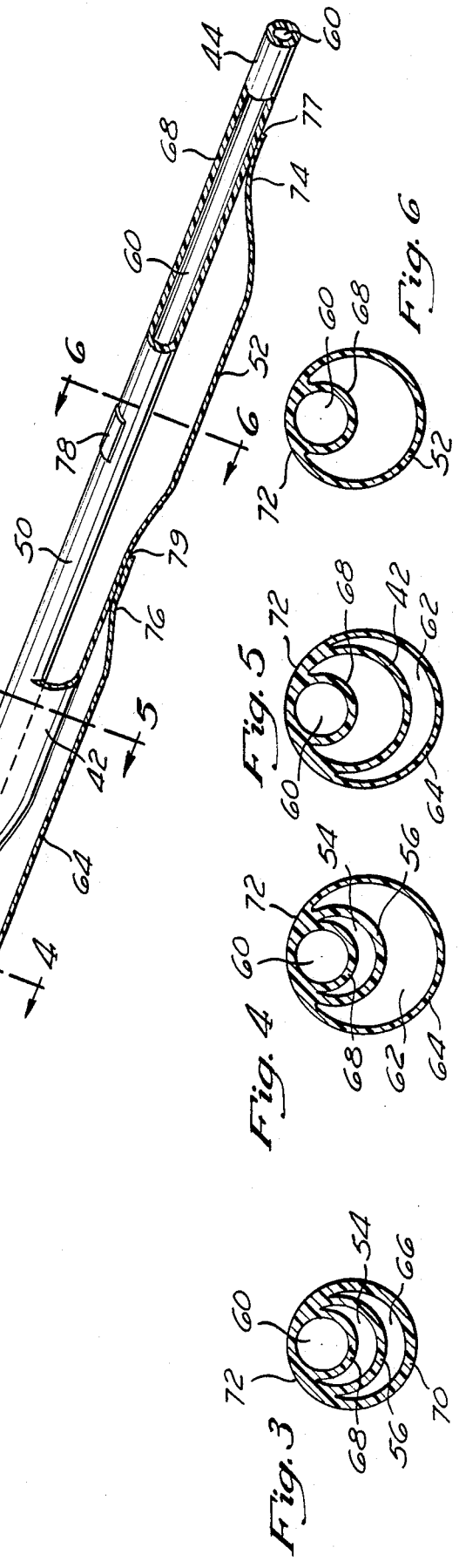

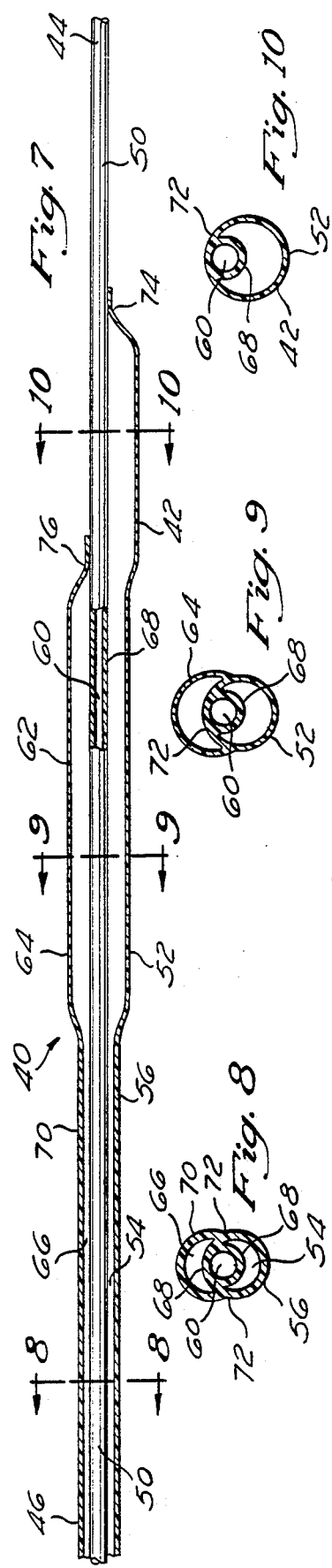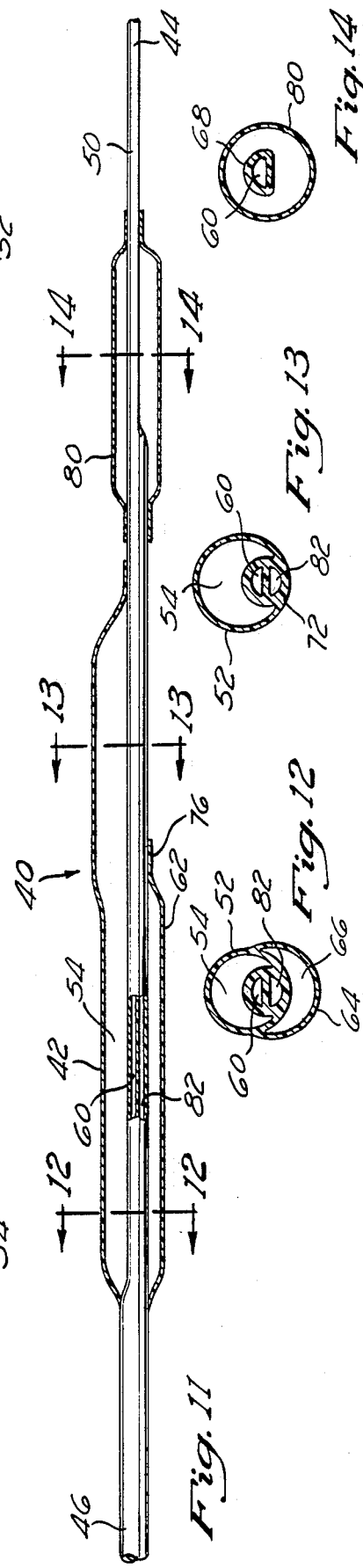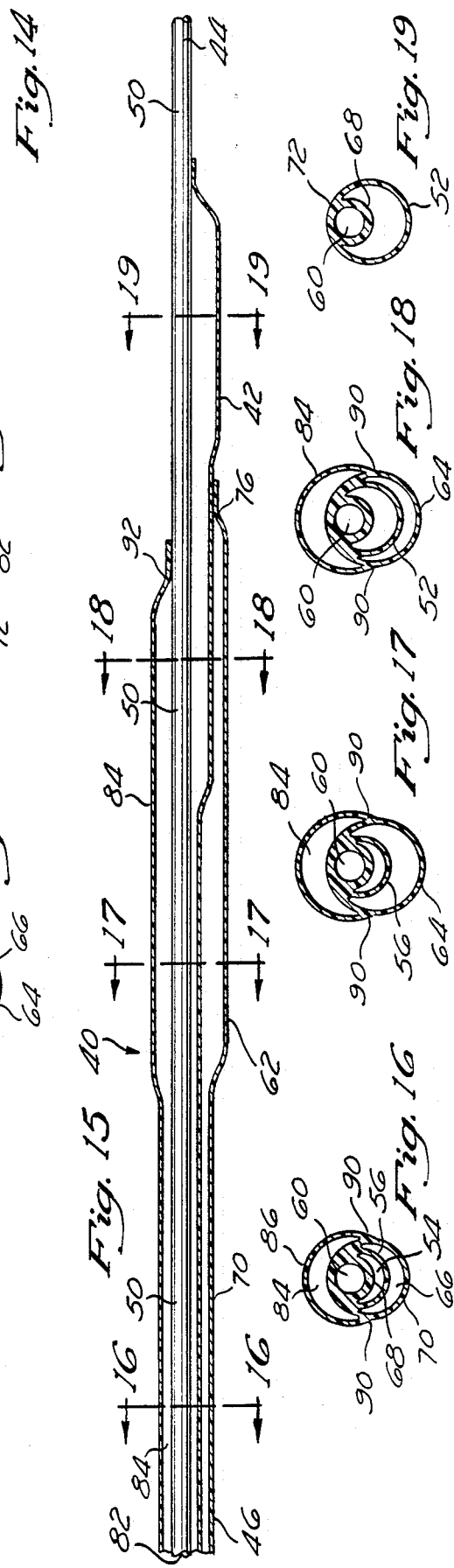

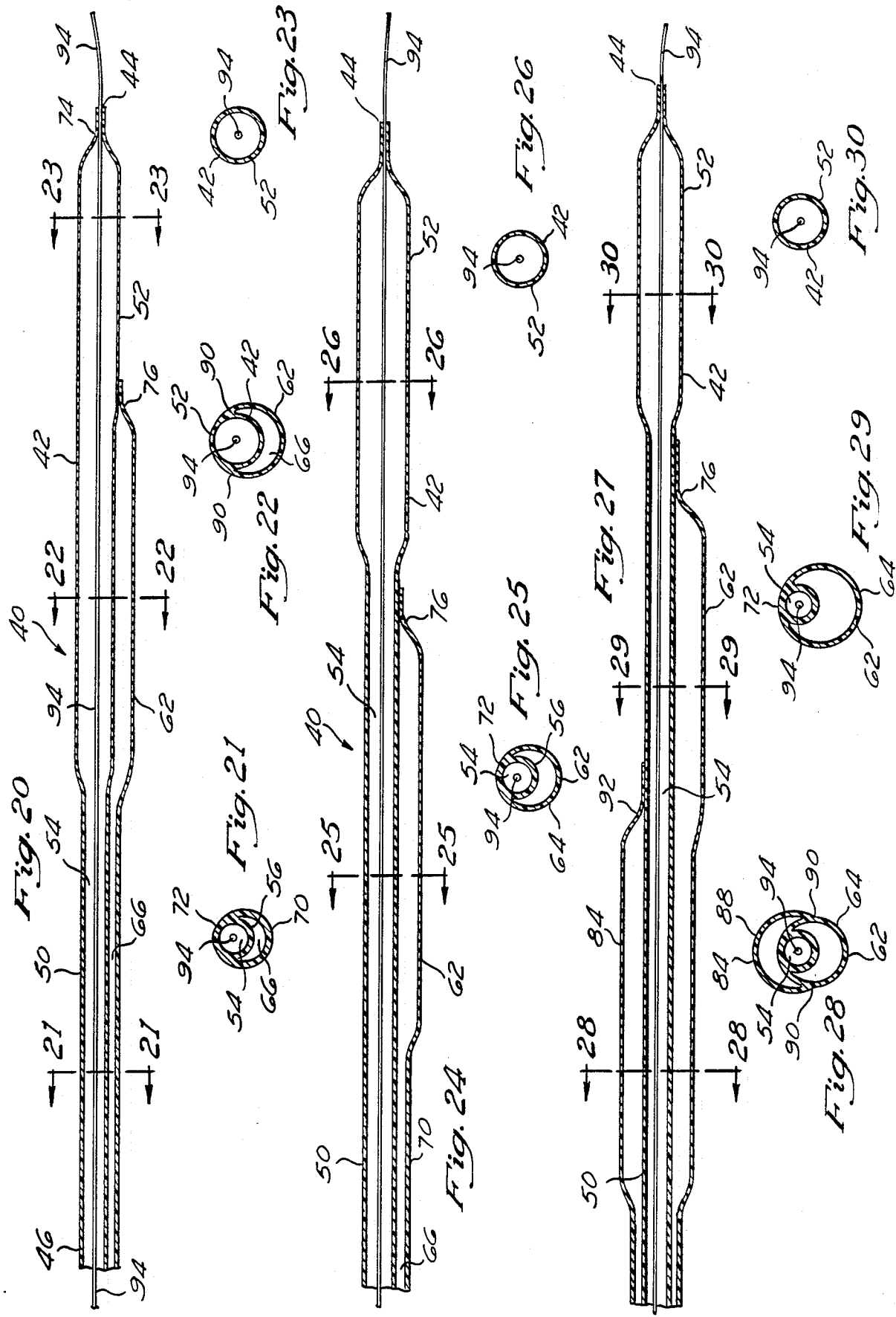

LIMACON GEOMETRY BALLOON ANGIOPLASTY CATHETER SYSTEMS AND METHOD OF MAKING SAME

BACKGROUND OF THE INVENTION

This invention relates to balloon angioplasty catheters having limacon geometry and a method of making same, and to angioplasty catheter systems utilizing multiple balloons, and to angioplasty procedures utilizing those catheters.

Coronary angioplasty has emerged as the only viable.. present alternative to bypass surgery for revascularization of stenotic and occluded coronary arteries. Although transluminal angioplasty has application in peripheral artery disease, it is most widely used in the treatment of coronary artery disease. Unlike bypass surgery, percutaneous angioplasty does not require general anesthesia, cutting of the chest wall, extracorporeal perfusion, or transfusion of blood. Percutaneous coronary angioplasty is not only less invasive and less traumatic to the patient, it is also less expensive because the angioplasty patient will have a shorter hospital stay and shorter post-procedure recovery time.

Percutaneous transluminal angioplasty is performed by making a skin puncture with a specially-designed needle in one of the groins, and then introducing a guiding catheter (typically 8 or 9 French size) into the aorta and coronary artery orifice. A smaller caliber catheter which has a built-in inflatable and deflatable balloon of predetermined size and diameter is passed through the guiding catheter which is positioned in the opening of a target artery. This balloon catheter (with the balloon totally deflated by negative pressure) is advanced inside the target artery toward the point of obstruction that needs to be dilated. With the balloon portion of the catheter properly positioned inside the obstructed segment of the artery, under X-ray fluoroscopic observation, the balloon is inflated by injecting contrast media mixed with saline at a pressure sufficient to overcome the resistance of the arterosclerotic plaque of the obstructed segment.

During the guiding catheter manipulation and especially while the balloon catheter is being advanced into the narrowed segment of the artery, X-ray fluoroscopy is used extensively. However, because one cannot ordinarily see the anatomy of an artery under X-ray fluoroscopy, contrast material is used. When contrast media is injected into an artery, details of the arterial anatomy are briefly visible until the contrast material flows away with the blood flow through the artery. Radiographic arteriograms are recorded during that brief moment of visualization. If the anatomic structures are complex and negotiating a particular arterial channel with the balloon catheter is difficult, frequent contrast injections during the procedure are necessary. However, there are limits to the amount of contrast material one can use in a given patient. For instance, the upper limit of Renografin-76 in a normal individual is approximately 3 c.c.'s per kilogram of body weight. The tolerance of a physically-ill individual may be substantially less. Excessive amounts of contrast material can be toxic to the kidneys, liver and brain.

By inflating the balloon in the stenosis multiple times over a period of between 20–30 seconds and one or two minutes (allowing blood flow between inflations), the desired dilation of the obstructed segment of the artery can be achieved. When the desired results have been obtained by balloon inflations, the guiding catheter and the balloon catheter (with the balloon completely deflated with negative pressure) are withdrawn from the artery and the procedure is successfully terminated.

Arterosclerotic coronary artery disease is not curable. Both bypass surgery and balloon angioplasty are considered palliative treatments. Recurrence of disease after bypass surgery or coronary angioplasty is prevalent, and repeat procedures are not uncommon due to the nature of the disease. A patient may initially develop single-vessel coronary artery disease and then slowly progress into multiple-vessel disease over the years. Medications, bypass surgery or angioplasty do help to relieve the symptoms, but they generally cannot prevent a gradual progression of the disease.

Because the cost of bypass surgery is 2 to 2.5 times the cost of angioplasty, and because bypass surgery is more invasive and more traumatic, requiring longer hospital stays and longer post-operative recuperation, future demand for angioplasty is expected to grow as physician skill and equipment technology expands. It has been estimated that the number of coronary artery angioplasties performed in the United States will double or triple to 450,000 or 500,000 cases per year by the early to mid 1990's. It also has been estimated that the number of multiple-vessel angioplasty cases will be from 2 to 2.5 times the number of single-vessel angioplasty cases. This will be a dramatic change from the situation in 1986 in which 70 to 80 percent of the coronary angioplasty cases are single-vessel dilations. The expected future growth of multi-vessel coronary angioplasty has serious technical and patient care implications. Present-day coronary angioplasty technology is based on the original single balloon concept which was designed to tackle single-vessel disease and thus single-vessel dilations. However, the single balloon technology is inadequate to meet the requirements of most multi-vessel disease situations.

During a typical coronary angioplasty, most of the procedure time is spent in certain preliminary steps that are necessary before the balloon can be inflated inside the obstructed segment of a target artery. In fact, the real job of dilating a vessel takes less than 20 percent of the total procedure time. The preliminary steps include patient (aseptic) preparation, groin preparation and needle puncture, insertion of the guidewire into the artery to introduce the guiding catheter, arterial heparinization, manipulation of the guiding catheter to cannulate the target coronary orifice, preliminary arteriography using contrast media injection into the artery and taking radiographic cine. Moreover, the balloon catheter must be prepared before it can be introduced into the target artery through the lumen of the guiding catheter. Preparation of the balloon catheter takes a minimum of 15–20 minutes. X-ray fluoroscopy and contrast media are extensively used during the guiding catheter and balloon catheter manipulations, especially when the balloon tip is being manipulated through the inside of the artery toward an obstructed segment which needs to be reopened by the balloon tip. Sometimes, the majority of the procedure time and the limits of the total allowable contrast volume are used up at this phase of a procedure It is clear from the medical literature that the longer the procedure, the greater the risk of complications during cardiac catheterization. Likewise, the larger the volume of contrast material, the greater the chance of kidney failure or tissue toxicity, including brain and/or liver damage.

The size and diameter of the balloon to be used in a transluminal angioplasty should be approximately matched to the size and native diameter of the obstructed segment of the artery to be dilated. If the balloon size and diameter is smaller than the native artery, the results of balloon angioplasty are suboptimal, requiring a second dilation with a larger-sized balloon. In some cases, the result is a failed procedure, which may require either a second separate angioplasty procedure (especially if too much contrast material was already used) or bypass surgery. If the balloon is oversized in relation to the obstructed segment of the native vessel, the inner wall of the artery may dissect from the remainder of the artery and may occlude the vessel completely, causing total cessation of blood flow to the target area of the myocardium. This complication, except in rare occasions, leads to acute myocardial infarction and necessitates emergency bypass surgery. If the acute occlusion leads to a large infarction, death is a possibility.

The most common balloon diameters in demand for coronary angioplasties are 2.0 mm, 2.5 mm, 3.0 mm and 3.5 mm. The 2.0 mm and 2.5 mm balloons are used in patients with small caliber coronary arteries or in the distal coronary branches of patients with otherwise normal-sized coronary arteries. However, a 1.5 mm balloon may also be desirable for certain applications. The 3.0 mm and 3.5 mm balloons are generally used in the proximal and larger native coronary arteries. If a patient has a single obstruction in the right or left coronary artery system, a single balloon catheter with a matching diameter and size will be selected for the intended dilation procedure. When the balloon is inflated inside the obstructed segment of the native artery, the balloon should maintain the original preshaped configuration and diameter under the maximum allowed pressure, which is generally up to 150 psi or more. Polymers such as PVC (polyvinylchloride) and various derivatives of polyethylene have proved to be suitable for making balloon catheters for coronary angioplasty. New polymer derivatives, including variations of Mylar material, are gaining popularity because of their high tensile strength and their potential for making very thin-walled dilation balloons.

In single lesion dilations, the choice of a properly-sized balloon catheter is relatively simple, although there are instances in which the original selection of the balloon catheter is inadequate so that a second balloon catheter is necessary to complete the procedure successfully. However, in multi-vessel disease, balloon catheter selection becomes compounded and complex. For example, a patient may have three lesions in his left coronary artery, and all three lesions may be approachable individually for successful balloon angioplasty But such lesions may be in vessels of different sizes, such as a 3.0 mm lesion in the proximal portion of the left anterior descending artery (LAD), a 2.0 mm lesion in the distal segment of the LAD, and a 2.5 mm lesion in the superior obtuse marginal artery. With currently available balloon catheters, angioplasty of these three differently-sized lesions is not always impossible, but it is cumbersome and inefficient. For each lesion, a matching balloon catheter is exchanged and manipulated into the target lesion under fluoroscopy with numerous contrast injections. To do this three times in a row requires roughly three times the procedure time, three times the contrast amount, and a minimum of three separate balloon catheters and their accessory devices. In light of the forecast that approximately two thirds of 450,000 to 500,000 patients in the 1990s will need multi-vessel coronary angioplasty, it is clear that there is a need for a major advance in balloon angioplasty that will provide more efficient and cost effective angioplasty balloon systems specifically designed (and suited) for multi-vessel coronary angioplasty.

In multiballoon angioplasty procedures, the smoothness and flexibility of the distal end of the angioplasty catheter are extremely important. Too much stiffness or rigidity in the balloon section at the distal end of the catheter makes insertion of the catheter more difficult. Smoothness of the catheter is also desirable and, in a multiple balloon catheter, it will be important to provide a smooth transition from balloon to balloon on the outside of the catheter.

Balloon fabrication techniques heretofore employed have significant disadvantages when it comes to multiple balloon catheters. Such difficulties include the difficulty of providing a smooth transition from balloon to balloon and difficulties in bonding balloons together in a lengthwise manner. Those difficulties are addressed by the present invention, which provides multiple balloon catheters adapted for use in multiple vessel disease. Such catheters have not heretofore been available and the need for an angioplasty procedure suitable for use in multivessel disease is readily apparent.

SUMMARY OF THE INVENTION

The present balloon angioplasty catheter invention provides an angioplasty catheter having multiple balloons that are integrally formed with the catheter shaft itself from a single, monolithic piece of polymer material. This provides for an extremely smooth transition from balloon to catheter shaft, and also minimizes the material present in the balloon portion of the catheter, thus providing increased flexibility for the catheter itself. The method for making the catheters of the present invention is well adapted for making multiple balloon catheters, and circumvents many of the complications that would be experienced in applying conventional balloon fabrication techniques heretofore used for single balloon catheters to multiple balloon catheter manufacture.

The present invention is designed for compatibility with existing and commercially available guidewires and guiding catheters, requiring, at most, minimal modification of those existing systems.

The balloons utilized in the present invention must meet stringent requirements that are unique to angioplasty balloons. They are: (a) the balloon must maintain its predetermined precise diameter and its original configuration under high inflation pressures (typically up to 150 psi or more) without significant or undue stretch or deformation; (b) the material used in construction of the balloon must have a high tensile strength and not rupture during inflation to the prescribed high pressure; (c) the balloon must be independently inflatable and deflatable under the external control of the operator; (d) the cross-sectional profile of the balloon should be low (0.90 mm to 1.20 mm or less in diameter) when it is deflated with negative pressure so that it can pass through the lumen of a guiding catheter and the tight and sometimes very hard internal lumen of the stenotic segment of a target artery; and (e) the material must be flexible as well as resilient so that the balloon catheter can negotiate the tortuous and sometimes irregular artery by following or advancing over a guidewire already placed in the artery ahead of the balloon catheter.

In all of the embodiments of the present invention, radiopaque markers may be provided on the catheter to mark the longitudinal location of any or all of the balloons on the catheter.

For coronary angioplasty, it is preferred that none of the balloons exceed about 40 mm in length, and most preferably none of the balloons exceed about 30 mm in length. For peripheral angioplasty, it is preferred that none of the balloons exceed about 100 mm in length, and they most preferably do not exceed about 80 mm in length. For coronary angioplasty, it is further preferred that the maximum inflated diameter of each of the balloons does not exceed about 4.5 mm. For peripheral angioplasty, it is preferred that the maximum inflated diameter of each of the balloons does not exceed about 15 mm, although larger diameters may be required for aortic use. Finally, for valvular angioplasty, it is preferred that none of the balloons exceed about 30 mm, preferably 25 mm, in diameter, and that they do not exceed 65 mm, preferably 60 mm, in length.

Thus, in accordance with one aspect of the present invention, there is provided an angioplasty catheter, comprising a catheter shaft having a proximal end and a distal end, an angioplasty balloon on the distal end of the catheter shaft, the balloon having a balloon wall and a length, wherein the balloon and the distal end of the catheter are formed from a single monolithic piece of polymer material and wherein the balloon is eccentrically positioned with respect to the catheter shaft, and at least two lumens in the catheter shaft, one of the lumens in communication with the interior of the balloon, and the other extending through the balloon and being suitable for receiving a steerable guidewire.

In accordance with another aspect of the present invention, there is provided an angioplasty catheter, comprising a catheter shaft having a proximal end and a distal end with at least two lumens extending therethrough, and an angioplasty balloon on the distal end of the catheter shaft, wherein the balloon and the distal end of the catheter shaft are formed from a single monolithic piece of polymer material by sealing shut the distal end of one of the lumens and heating the distal end of the catheter shaft, then internally pressurizing the sealed lumen to expand at least a portion of the distal end of the catheter shaft into the balloon, wherein the balloon is eccentric with respect to the catheter shaft.

In accordance with another embodiment of the present invention, there is provided an angioplasty catheter, comprising a catheter shaft having a proximal end and a distal end, at least two independently inflatable and independently deflatable angioplasty balloons at the distal end of the catheter, each balloon having a balloon wall and having a length and a maximum inflated diameter, wherein the balloons and the distal end of the catheter shaft are formed from a single, monolithic piece of polymer material and wherein the balloons are eccentrically positioned with respect to each other. The balloons may advantageously also be eccentric with respect to the catheter shaft. Moreover, the wall of each balloon may be joined to either another of the balloons or to the catheter shaft along substantially the entire length of each balloon.

It is preferred that maximum inflated diameter of each balloon is substantially uniform over the length of the balloon when measured together with the thickness of any overlying, uninflated balloon.

In one preferred embodiment, the balloons comprise a first balloon and a second balloon, and the maximum inflated diameter of the first balloon is less than the maximum inflated diameter of the second balloon. The first balloon may be at least partially inside the second balloon, and preferably at least 15% but less than 85% of the length of the first balloon is inside the second balloon. In an alternative embodiment, the first balloon is distal of the second balloon. The first balloon and the second balloon are located on the same side of the catheter shaft, or on opposite sides.

In yet another embodiment of the invention, the balloons comprise a first balloon and the second balloon and further comprise a third balloon on the catheter shaft. Two balloons may be on the same side of the catheter shaft and the other balloon may be on the opposite side of the catheter shaft; alternatively, the balloons may all be on the same side of the catheter shaft.

In yet another embodiment of the invention, the catheter shaft extends through the balloons, and the catheter shaft has a lumen extending the length of the catheter shaft for receiving a steerable guidewire.

In still another embodiment of the invention, the catheter shaft includes at least a first lumen and a second lumen extending through the catheter shaft, and the balloons comprise a first balloon and a second balloon, wherein the first lumen terminates inside the first balloon and the second lumen terminates inside the second balloon. In this embodiment, the catheter further comprises an axial torque guidewire extending through the first lumen and out of the distal end of the first balloon and the catheter, wherein the distal end of the first balloon is sealed to the guidewire. The walls of the first balloon may be formed by expanding the walls of the first lumen and the first balloon may be substantially coaxial with the first lumen. Moreover, the walls of the second balloon may be formed by expanding the walls of the second lumen and the second balloon may be eccentric with respect to the second lumen. The catheter may still further comprise a third balloon and the catheter shaft may have a third lumen in communication with and terminating inside the third balloon, wherein the third balloon is eccentric with respect to the third lumen.

In any of the catheters disclosed herein, the walls of each balloon may be joined to a common line on the catheter shaft along substantially the entire length of each balloon. Alternatively, the wall of the first balloons may be joined to the catheter shaft along a line extending substantially the length of the first balloon and the wall of the second balloon may be joined to the wall of the first balloon along a line extending along the length of the first balloon. Moreover, each balloon has a proximal end and a distal end, and the distal end of one of the balloons may be joined to the wall of another of the balloons.

In accordance with another aspect of the present invention, there is provided a method for making angioplasty balloons, comprising the steps of forming from a single piece of polymer material a length of catheter shaft material having at least a first lumen and a second lumen therein, each lumen having an outer wall, each lumen having a proximal end and a distal end, sealing the distal end of the first lumen to form a first sealed lumen, and applying pressure to the proximal end of the first sealed lumen and heating the outer wall thereof to expand the first sealed lumen inside a first die to expand the outer wall of the first sealed lumen to form a first balloon therefrom having dimensions determined by the dimensions of the interior of the die. The method may further comprise the steps of sealing the distal end of the second lumen to form a second sealed lumen, applying pressure to the proximal end of the second sealed lumen and heating the outer wall thereof to expand the second sealed lumen inside a second die to form a second balloon therefrom having dimensions determined by the dimensions of the interior of the second die, wherein the first balloon and the second balloon are eccentric with respect to each other. The sealed end of the first lumen may be located distally of the sealed end of the second lumen so that the distal end of the first balloon is located distally of the distal end of the second balloon. In one embodiment, the outer wall of the first lumen is located inside the outer wall of the second lumen. In another embodiment, the first balloon and the second balloon are located on opposite sides of the catheter The forming step may advantageously be a molding step or an extrusion step. When the forming step is an extrusion step, the method may further comprise the step of shortening the second lumen prior to sealing the distal end thereof by removing a length of the outer wall of the second lumen at the distal-most end of the second lumen so that the distal end of the second lumen is located proximally of the distal end of the first lumen In one embodiment of the method, the sealing step for the second lumen comprises bonding the outer wall of the second lumen at the distal end thereof to the outer wall of the first lumen.

In each embodiment of the method, the catheter shaft material may further have a third lumen therein, and the method may further comprise the steps of sealing the distal end of the third lumen to form a third sealed lumen, and applying pressure to the proximal end of the third sealed lumen and heating the outer wall thereof to expand the outer wall of the third sealed lumen inside a die to form a third balloon therefrom having dimensions determined by the dimensions of the interior of the die.

BRIEF DESCRIPTION OF THE DRAWINGS

FIG. 1 is a side elevation of the distal end of a dual-balloon steerable guidewire limacon geometry angioplasty catheter having balloons on the same side of the guidewire lumen showing the balloons and connecting lumens in longitudinal section and the guidewire lumen in partial cross section.

FIG. 2 is a perspective view of the distal end of the catheter of FIG. 1, partially in cross section.

FIG. 3 is a cross section of the catheter of FIG. 2, taken along the line 3—3.

FIG. 4 is a cross section of the catheter of FIG. 2, taken along the line 4—4.

FIG. 5 is a cross section of the catheter of FIG. 2, taken along the line 5—5.

FIG. 6 is a cross section of the catheter of FIG. 2, taken along the line 6—6.

FIG. 7 is a side elevation of the distal end of a steerable guidewire dual balloon catheter of the present invention having balloons on opposite sides of the catheter shaft, with balloon lumens and balloons shown in longitudinal section and with the guidewire lumen shown in partial cross section.

FIG. 8 is a cross section of the catheter of FIG. 7, taken along the line 8—8.

FIG. 9 is a cross section of the catheter of FIG. 7, taken along the line 9—9.

FIG. 10 is a cross section of the catheter of FIG. 7, taken along the line 10—10.

FIG. 11 is a side elevation of the distal end of a triple balloon steerable guidewire catheter of the present invention, having integrally-formed balloons on opposite sides of the guidewire lumen, with balloons shown in longitudinal section and with the guidewire lumen and the distal balloon lumen shown in partial section.

FIG. 12 is a cross section of the catheter of FIG. 11, taken along the line 12—12.

FIG. 13 is a cross section of the catheter of FIG. 11, taken along the line 13—13.

FIG. 14 is a cross section of the catheter of FIG. 11, taken along the line 14—14.

FIG. 15 is a side elevation of a triple balloon steerable guidewire catheter of the present invention, having two overlapping balloons on one side of the guidewire lumen, and another balloon on the opposite side of the guidewire lumen, with the balloon lumens and balloons shown in longitudinal section.

FIG. 16 is a cross section of the catheter of FIG. 15, taken along the line 16—16.

FIG. 17 is a cross section of the catheter of FIG. 15, taken along the line 17—17.

FIG. 18 is a cross section of the catheter of FIG. 15, taken along the line 18—18.

FIG. 19 is a cross section of the catheter of FIG. 15, taken along the line 19—19.

FIG. 20 is a side elevation of the distal end of an axial torque guidewire overlapping double balloon catheter of the present invention, with the balloons and the catheter shaft shown in longitudinal section.

FIG. 21 is a cross section of the catheter of FIG. 20, taken along the line 21—21.

FIG. 22 is a cross section of the catheter of FIG. 20, taken along the line 22—22.

FIG. 23 is a cross section of the catheter of FIG. 20, taken along the line 23—23.

FIG. 24 is a side elevation of the distal end of a tandem dual balloon axial torque guidewire catheter of the present invention, showing the catheter shaft and balloons in longitudinal section.

FIG. 25 is a cross section of the catheter of FIG. 24, taken along the line 25—25.

FIG. 26 is a cross section of the catheter of FIG. 24, taken along the line 26—26.

FIG. 27 is a side elevation of a triple balloon axial torque guidewire catheter of the present invention, with the balloons and catheter shaft shown in longitudinal section.

FIG. 28 is a cross section of the catheter of FIG. 27, taken along the line 28—28.

FIG. 29 is a cross section of the catheter of FIG. 27, taken along the line 29—29.

FIG. 30 is a cross section of the catheter of FIG. 27, taken along the line 30—30.

DETAILED DESCRIPTION OF THE INVENTION

Figure 31:
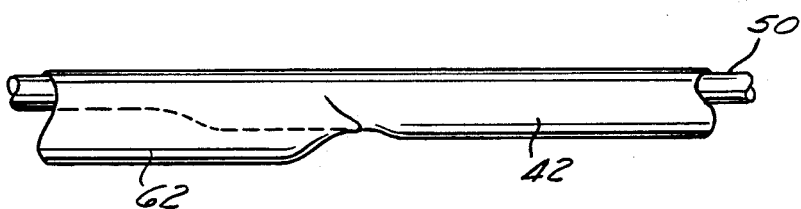
FIG. 31 is a side elevation of a portion of the balloon segment of a catheter of the type illustrated in FIG. 2, showing one embodiment of a joint between two balloons.

The angioplasty catheters of the present invention fall into two broad, general categories: steerable guidewire type catheters and axial torque guidewire-type catheters. Both steerable guidewire catheters and axial torque guidewire catheters are known in the art. Briefly, a steerable guidewire-type catheter has a guidewire lumen extending the entire length of the catheter, from the proximal end to the distal end thereof, and the guidewire lumen extends through or past all of the balloons. A guidewire can be threaded through the lumen and is rotatable through the lumen. An axial torque guidewire-type catheter, on the other hand, has a guidewire that extends through a lumen that terminates inside the distal-most balloon, and the guidewire extends out from the distal end of the distal-most balloon. The distal-most end of the balloon is bonded directly to the guidewire so that rotation of the proximal end of the guidewire about its axis rotates the guidewire tip to permit selection of a target vessel.

In general, the balloons of the present invention share a number of characteristics in common with conventional angioplasty balloons. These characteristics differentiate angioplasty balloons from other types of known catheter balloons. Angioplasty balloons are generally cylindrical and have a predetermined maximum inflated diameter that remains more or less constant over the range of working pressures to which the balloon is subjected. Modern balloon materials can be inflated with pressures of at least 100 psi, preferably at least 150 psi, and often 200 psi. The balloon wall is not resilient, elastic material, but instead is folded against the catheter shaft in its deflated state and, upon inflation, assumes a predetermined shape. Even when inflation pressures reach the high values discussed herein, only a minor amount of stretching, if any, occurs. The hard, non-elastic balloon, when inflated, has the ability to compress sclerotic lesions or stretch the narrowed segments in order to increase blood flow through a diseased blood vessel.

The angioplasty catheters of the present invention are suitable for coronary angioplasty, peripheral angioplasty, and valvular angioplasty. The angioplasty balloons may be provided in different diameters and lengths, depending on the intended use of the catheter. Balloon catheter shafts of size French 4.0 or less are preferred. For coronary angioplasty, balloon diameters of from about 1.0 mm to about 4.0 mm and lengths from about 7 mm to about 30 mm are preferred. For peripheral vascular angioplasty and valve angioplasty, the balloons may have diameters between about 3.0 mm and about 20 mm, with lengths between about 25 mm and about 60 mm.

Any of a number of materials may be used to make the balloon catheters of the present invention. At least the distal end of the catheter and the balloons are preferably formed from high-strength thermoplastic material, which may be the same as conventional angioplasty balloon materials or may be other, advanced thermoplastic materials. Balloon materials that have been used or are now in use include polyvinylchloride, polyethylene, polyethylene terephthalate (PET) mylar brand polyester material (made by du Pont). Other suitable film-forming materials capable of withstanding pressures of 100 psi, preferably 150 psi or 200 psi, without bursting or significant stretching, may also be used to form the distal end of the catheter and the angioplasty balloons.

The catheters of the present invention are typified by the dual balloon catheter illustrated in FIGS. 1 and 2. To the extent that the catheters retain common or comparable elements from Figure to Figure, the same numbering will be applied to such elements, which will not always be separately explained for each Figure.

The catheters of the present invention are referred to as having "limacon" geometry because of the resemblance of the cross section of the catheter to a limacon. It will be understood, however, that the catheters of the present invention are not required to exhibit true limacon geometry in cross section.

I. Steerable Guidewire-Type Limacon Geometry Catheters

With respect to FIGS. 1 and 2, a catheter 40 has at least one balloon, the first balloon 42 at the distal end 44 of the catheter 40. The catheter 40 also has a proximal end 46 which is indicated at the far left-hand side of FIG. 2; however, it will be understood that the proximal end 46 of the catheter 40 is the end at the extreme opposite end of the catheter 40 from the distal end 44, and that the true proximal end 46 is not shown in FIG. 2. Rather, FIG. 2 illustrates only the distal balloon-bearing portion of the catheter 40, and the reference numeral 46 is provided only for purposes of indicating the proximal direction.

The catheter 40 also has a catheter shaft 50 on which a first balloon 42 is formed. As used herein, the catheter shaft 50 shall refer to the lumens and their walls in an expanded state. The catheter shaft 50 shall not be considered to include outer walls of lumens which have been expanded into balloons. The first balloon 42 has a first balloon wall 52. A first lumen 54 having an outer wall 56 extends from the proximal end 46 of the catheter 40 to the interior of the first balloon 42, providing a fluid passageway between the proximal end 46 of the catheter 40 and the interior of the first balloon 42.

The catheter shaft 50 is also provided with a guidewire lumen 60 through which a steerable guidewire may be passed. The guidewire lumen has an outer wall 68 and extends from the proximal end 46 of the catheter shaft 50 to the distal end 44 of the catheter 40, and is large enough to receive a conventional steerable guidewire and to further permit monitoring of blood pressure trough the guidewire lumen 60. The guidewire lumen 60 and any guidewire placed therethrough extend beyond the distal-most end of any of the balloons, such as first balloon 52, on the catheter 40. The guidewire lumen 60 of the catheter 40 preferably has an inner diameter of about 0.014 to about 0.016 inches, just large enough to accommodate a 0.012 or 0.014 inch conventional steerable guidewire inside and to monitor distal pressure through the lumen. The outside diameter of the catheter shaft 50 at the proximal end 46 of the catheter 40 should be size French 4.0 or less. In all of the steerable guidewire catheters of the present invention, holes communicating with the guidewire lumen 60 may be provided just proximally of the balloons to permit blood flow through the guidewire lumen 60 and past the balloons 42, 62, to maintain coronary perfusion during balloon inflation.

A second balloon 62 having a wall 64 is also provided on the catheter shaft 50. A second lumen 66 having an outer wall 70 extends through the catheter shaft from the proximal end 46 thereof to the interior of the second balloon 62 to provide fluid communication between the proximal end 46 of the catheter 40 and the second balloon 62.

At least the portion of the catheter 40 illustrated in FIG. 2, from a point just proximally of the balloons 42, 62, including the catheter shaft 50, the walls 56, 70 of the lumens 54, 66, and the walls 52, 64 of the balloons 42, 62, is all formed from a single, monolithic piece of polymer material. Thus, the outer wall 56 of the first lumen 54 has been enlarged and stretched to form the wall 52 of the first balloon 42. Similarly, the outer wall 70 of the second lumen 66 has been enlarged and stretched to form the wall 64 of the second balloon 62. It should be understood that the thickness of the balloon walls 52, 64 is generally between about 0.01 mm and 0.10 mm, depending on the strength and flexibility of the material from which the balloons 42, 62 are formed. This thickness is greatly exaggerated in all of the figures for purposes of illustration only. Moreover, the thickness of the outer walls 56, 70 of the lumens 54, 56 is substantially greater than the thickness of the balloon walls 52, 64. The outer walls 56, 70 of the lumens 54, 66 are rigid enough to maintain their dimensions when negative pressure is applied to the proximal end of the lumens 54, 66. In contrast, the very thin balloon walls 52, 64 are flexible and readily collapse when negative pressure is applied to the appropriate lumen for each balloon.

The guidewire lumen 60 has an outer wall 68. As illustrated in FIG. 3, each of the outer walls 56, 68, 70 of the lumens 54, 60, 66 converge to a common point or line into a common wall 72. Thus, the common wall 72 is a convergence point for outer lumen walls 56, 68, 70. The lumen walls 56, 68, 70, 72 in radial cross section, as shown in FIG. 3, are arranged as eccentric circles, one within another, longitudinally joined together at the common lumen wall 72. The common lumen wall 72 is a line running the length of the catheter shaft 50.

The balloon arrangement in the dual balloon limacon geometry catheter 40 of FIGS. 1 and 2 is a partial overlap design. That is, the first balloon 42 is partially inside the second balloon 62. The distal end 74 of the first balloon 42 is joined to the outer wall 68 of the guidewire lumen 60. The distal end 76 of the second balloon 62 is joined semicircularly to the underlying wall 52 of the first balloon 42. The joints 77, 79 between the distal ends 74, 76 of the first and second balloons 42, 62 and the underlying structure, are formed using any suitable balloon joint bonding process, such as heat bonding, vulcanization bonding, solvent bonding, ultrasonic welding, laser welding, and glue bonding. These balloon joints are semicircular around the catheter shaft; thus, substantially the entire distal ends 74, 76 of the first and second balloons 42, 62 are closed. The joint itself in all of the balloon designs may lie in a plane normal to the axis or length of the catheter shaft 50, or it may preferably lie in a plane at an acute angle to the length of the catheter shaft 50.

The first balloon 42 may be completely inside the second balloon 62; however, it is preferred that the first balloon 42 be only partially inside the second balloon 62. In a preferred embodiment, at least 15% of the length of the first balloon 42 is inside the second balloon 52, but less than 85% of the length of the first balloon 42 is inside the second balloon 62. It should be understood, however, that the design of FIG. 2 may be modified to provide a tandem dual-balloon limacon geometry catheter, wherein the entire first balloon 42 is located distally of the second balloon 62. In the tandem design, the first balloon 42 is completely outside the second balloon 62.

Under ordinary conditions of use, when one of the balloons 42, 62 is inflated, the other balloon will be deflated. (Both balloons 42, 62 are shown in the inflated configuration simply for purposes of illustration.) Although the wall 64 of the outer balloon 62 is very thin, it is nevertheless tangible. In a preferred embodiment of the present invention, in order for the effective maximum inflated working diameter of the first balloon 42 to be uniform along substantially its entire length, the diameter of the portion of the first balloon 42 that is inside the second balloon 62 is slightly less than the diameter of the portion of the first balloon 42 that is outside the second balloon 62, with the difference in diameters between the two portions of the balloon 42 being approximately equal to the thickness of the overlying, uninflated second balloon 62. In this way, the maximum inflated effective working diameter of the first balloon 42, together with any overlying uninflated balloon walls, is substantially uniform along the entire length of the first balloon 42.

In one alternative embodiment of the present invention which may be applied to any of the designs falling within the scope of the present invention, radiopaque markers 78 may be provided on the catheter shaft 50 so the location of the catheter may be radiographically monitored.

The balloon construction may be more fully understood by comparison of the cross-sectional FIGS. 3-6. In the cross section of the second balloon 62 and the catheter shaft 50 illustrated in FIG. 4, the first lumen 54, its outer wall 56, the guidewire lumen 60, its outer wall 68, and the common wall 72 are substantially the same as in FIG. 3. However, the outer wall 70 of the second lumen 66 shown in FIG. 3, has, in FIG. 4, become the wall 64 of the second balloon 62.

In FIG. 5, a cross section through the catheter shaft 50 and both the first balloon 42 and the second balloon 62, the common wall 72, the guidewire lumen 60, and its outer wall 68 are substantially the same as in FIGS. 3 and 4. However, the outer wall 56 of the first lumen 54 in FIGS. 3 and 4 has been expanded to form the wall 52 of the first balloon 42, and the outer wall 70 of the second lumen 66 in FIG. 3 has become the wall 64 of the second balloon 62.

In FIG. 6, which is a cross section through only the first balloon 42 and the catheter shaft 50, taken distally of the second balloon 62, only the guidewire lumen 60, its outer wall 68, and the common wall 72 remain the same as illustrated in FIG. 3. The wall 52 of the first balloon 42 converges with the outer wall 68 of the guidewire lumen 60 at the common wall 72, which common wall 72 runs the entire length of the catheter 40. The wall 64 of the second balloon 62 (and/or the wall 70 of the second lumen from which it was formed) has been removed from the distal-most end of the catheter 40, and is not present in FIG. 6, the second balloon 62 having terminated proximally of the line 6—6.

The balloons 42, 62 in FIGS. 1 and 2 are eccentric with respect to each other and with respect to the catheter shaft 50 and the guidewire lumen 60. However, both the first balloon 42 and the second balloon 62 are located on the same side of the catheter shaft 50.

The first balloon 42 has a maximum inflated diameter that is less than that of the second balloon 62. The maximum inflated diameter of the first balloon 42 is preferably about 1.5, 2.0, 2.5, or 3.0 mm. The maximum inflated diameter of the larger, second balloon 62 is preferably 2.5 mm, 3.0 mm, 3.5 mm or 4.0 mm. The lengths of each of the balloons may advantageously be between about 15 mm and about 40 mm, preferably about 20 mm to about 25 mm.

Another dual balloon limacon-geometry steerable guidewire angioplasty catheter is illustrated in FIG. 7. The catheter 40 has a first balloon 42 on one side of the catheter shaft 50, and a second balloon 62 on the opposite side of the catheter shaft 50. A guidewire lumen 60 having an outer wall 68 on either side of common wall 72 runs the length of the catheter 40 and completely through the two balloons 42, 62.

The catheter of FIG. 7 differs from the catheters of FIGS. 1 and 2 because the balloons 42, 62 are on opposite sides of the catheter shaft 50 and the guidewire lumen 60.

A first lumen 54 and a second lumen 66 extend from the proximal end 46 of the catheter 40 into the interior, respectively, of the first balloon 42 and the second balloon 62 for independent inflation and deflation of the balloons 42, 62.

The outer wall 56 of the first lumen 54 becomes the wall 52 of the first balloon 42, and the outer wall 70 of the second lumen 66 becomes the wall 64 of the second balloon 62.

In FIG. 8, which illustrates a cross section of the catheter shaft 50 of the catheter of FIG. 7 taken proximally of the balloons 42, 62, it can be seen that the outer wall 56 of the first lumen 54 merges with the outer walls 68 to form two common walls 72. The outer wall 70 of the second lumen 66 merges with and is connected to the outer wall 56 of the first lumen 54 at a point adjacent to the common walls 72.

In FIG. 9, a cross section through both the first balloon 42 and the second balloon 62, together with the guidewire lumen 60, the outer walls 56, 70 of the first and second lumens 54, 66 have become the walls 52, 64 of the first and second balloons 42, 62. Only the guidewire lumen 60, its outer wall 68, and the common wall 72 remain the same as in FIG. 8.

In FIG. 10, a cross section taken through the first balloon 42 distally of the distal end 76 of the first balloon 72, only the wall 52 of the first balloon 42 and the central lumen 60 and its walls 68, 72 remain the same as in FIG. 9.

The diameters of the first and second balloons 42, 62 in FIG. 7 may advantageously be about the same as the diameters of the first and second balloons 42, 62 in the catheter illustrated in FIG. 2. However, in this design, the first balloon 42 is longer than the second balloon 62. Thus, although the proximal ends of the first and second balloons 42, 62 are at substantially the same point along the length of the catheter 40, the distal end 76 of the second balloon 62 is located proximally of the distal end 74 of the first balloon 42. The length of the first balloon 42 is preferably 25–45 mm, most preferably about 30 mm, and the length of the second balloon 62 is preferably 15–30 mm, preferably about 20 mm. Thus, the length of the first balloon 42 is greater than the length of the second balloon 62 by about 10 mm.

When the second balloon 62 is deflated and the first balloon 42 is inflated, the maximum inflated diameter of the first balloon 42 distally of the distal end 76 of the second balloon 62 is slightly greater than the maximum inflated diameter of the first balloon 42 proximally of the distal end 76 of the second balloon 62 by an amount substantially equal to the thickness of the deflated balloon 62. In this way, the effective maximum inflated diameter of the first balloon 42 is substantially uniform along the entire length of the first balloon 42, when taken together with the thickness of the overlying deflated second balloon 62.

The catheter illustrated in FIG. 7 has three effective working diameters. The first is the diameter of the first balloon 42, the second is the maximum inflated diameter of the second balloon 62, and the third effective diameter of the catheter of FIG. 7 is achieved by inflating both the first balloon 42 and the second balloon 62.

The catheter of FIG. 11 is a steerable guidewire catheter that has a first balloon 42 and a second balloon 62 generally as described in connection with FIG. 7. However, unlike the catheter of FIG. 7, the catheter of FIG. 11 includes a separate, non-unitary third balloon 80 located distally of the first balloon 42 and the second balloon 62. The separate third balloon 80 is separately formed and connected to the catheter shaft 50; it is not formed from the same monolithic piece of polymer material as are the first and second balloons 42, 62 and the catheter shaft 50.

In addition to the first lumen 54, the second lumen 66, and the guidewire lumen 60 described in connection with FIG. 7 and FIG. 2, the catheter of FIG. 11 has a third lumen 82 extending from the proximal end 46 of the catheter 40 to the interior of the third balloon 80 for independently inflating and deflating the third balloon 80.

In the catheter of FIG. 11, the first, second, and third balloons 42, 62, 80 are eccentric with respect to each other and the first and second balloons 42, 62 are eccentric with respect to the catheter shaft 50. Although in FIG. 11 the proximal end of the first balloon 42 is located at the same point as the proximal end of the second balloon 62, it should be understood that the proximal end of the first balloon 42 may instead be located distally of the proximal end of the second balloon 62.

The third balloon 80 is substantially coaxial with the catheter shaft 50 and is made from a tube of suitable balloon material which may be the same as or different from the material from which the first balloon 42 and the second balloon 62 are made. The third balloon 80 is bonded to the catheter shaft 50 by any conventional means, such as heat bonding, RF bonding, laser bonding, solvent welding, adhesive bonding, heat-shrink bonding, or other suitable technique.

The maximum inflated diameter of the third balloon 80 is preferably less than the maximum inflated diameter of the first balloon 42 and the second balloon 62. For coronary angioplasty, the third balloon 80 may have a maximum inflated diameter of about 2.0 mm and may be about 12–25 mm in length, preferably about 17 mm, the first balloon 42 may be from about 20 to about 30 mm in length, preferably about 25 mm, with a maximum inflated diameter of about 2.5 mm, and the second balloon 62 may be about 12–20 mm in length, preferably about 17 mm, with a maximum inflated diameter of about 3.0 mm. In another embodiment of this same catheter, the aforementioned maximum inflated diameters may each be increased or decreased by about 0.5 mm.

As shown in FIG. 12, a cross section through both the first balloon 42, the second balloon 62, and the catheter shaft 50, appears substantially the same as FIG. 9, except that a second lumen 82 is present. FIG. 13 similarly corresponds to FIG. 10, differing from FIG. 10 by the inclusion of the third lumen 82.

In FIG. 14, a cross section through the third balloon 80, only the central lumen 60, the outer wall 68 thereof, and the third balloon 80 are present.

Yet another catheter according to the present invention is illustrated in FIG. 15. This catheter is a triple balloon steerable guidewire catheter in which all three balloons are formed from the same monolithic piece of polymer material.

The catheter of FIG. 15 has a first balloon 42 and a second balloon 62, with the first balloon 42 partially inside the second balloon 42. The detailed description provided in connection with the catheter disclosed in FIG. 2 will not be repeated with respect to FIG. 15., only the structure added to the catheter of FIG. 2 will be emphasized.

In addition to the first balloon 42 and the second balloon 62 illustrated in FIG. 2, the catheter of FIG. 15 has a unitary third balloon 84 on the opposite side of the catheter from said first and second balloons 42, 62. A third lumen 82 is provided in the catheter shaft 50 in fluid communication with the interior of the third balloon 84. The third lumen 84 has an outer wall 86 which, as illustrated in cross section FIG. 16, is attached to the outer wall 70 of the third lumen 66 at two wall-to-wall junctions 90. The wall-to-wall junctions 90 run from the proximal end 46 of the catheter 40 to the distal end 92 of the third balloon 84.

The proximal ends of the second balloon 62 and the third balloon 84 are at roughly the same point along the length of the catheter shaft 50. The distal ends 76, 92 of the second balloon 62 and the third balloon 84 may also be located at roughly the same point along the length of the catheter shaft 50; however, a slightly offset relationship as illustrated in FIG. 15 is preferred. The catheter will generally be stiffer and/or bulkier at the distal end of a balloon because of the joint located at that point. Therefore, a smoother more flexible catheter results if the distal ends 76, 92 are slightly (or greatly) offset, rather than terminating at exactly the same point along the length of the catheters. In FIG. 15, two balloons 42, 62 are on one side of the catheter shaft 50 and one balloon 84 is on the other side of the catheter shaft 50.

FIG. 17 differs from FIG. 16 in that the outer walls 70, 86 of the second and third lumens 66, 82 have been expanded to form the second balloon 62 and the third balloon 84. As were the lumen walls 70, 86 from which they were formed, the second and third balloons 62, 84 are joined together along their length at the wall-to-wall junctions 90, which extend to the distal ends 76, 92 of those balloons 62, 84.

FIG. 18, a cross section through all three balloons 42, 62, 84, differs from FIG. 17 only in that the outer wall 56 of the first lumen 54 has become the wall 52 of the first balloon 42.

In FIG. 19, a cross section through only the first balloon 42, the catheter at that point comprises only the wall 52 of the first balloon 42 and the central lumen 60 with its walls 68 and 72.

The first balloon 42, the second balloon 62, and the third balloon 84 may advantageously be approximately the same length, preferably between about 12 mm and about 25 mm, more preferably about 17 mm, with diameters, respectively, of 2.0 mm, 2.5 mm and 3.0 mm. In other embodiments of the invention, the respective diameters of the three balloons 42, 62, 84 may be increased or decreased 0.5 mm.

II. Axial Torque-Type Limacon Geometry Catheters

FIG. 20 illustrates an axial torque-type limacon geometry multiple balloon catheter. In the illustrated dual balloon model, the catheter 40 has a first balloon 42 near the distal end 44 of the catheter 40. The catheter shaft 50 extends only to the proximal end of the first balloon 42. A first lumen 54 extends from the proximal end 46 of the catheter 40 to the interior of the first balloon 42 to provide for independent inflation and deflation of the first balloon 42.

A second balloon 62 may be provided on one side of the catheter shaft 50 and the first balloon 42. The second balloon 64 is connected to the proximal end 46 of the catheter 40 by a second lumen 66 running from the proximal end 46 of the catheter to the interior of the second balloon 62. The distal end 76 of the second balloon 62 is joined to the wall 52 of the first balloon 42.

An axial torque steel wire 94 runs the length of the catheter 40 from the proximal end 46 to the distal end 44 thereof. The axial torque steel wire 94 is preferably tapered from a proximal diameter of about 0.016 inches to a diameter at the distal tip thereof of about 0.008 inches. The distal end 74 of the first balloon 42 is bonded directly to the axial torque wire 94 by conventional bonding means, such as adhesive bonding, heat bonding, heat-shrink bonding, or other technique. The tip of the torque wire is welded to a short guidewire at the distal end of the catheter 40. No guidewire lumen 60 separate from the first lumen 54 is provided in this design.

Because an axial torque limacon catheter having dual balloons may be made with as few as two lumens, the catheter shaft 50 may be of relatively small diameter. Moreover, because there is no catheter shaft running through the first balloon 42, the balloon can collapse against the axial torque wire to provide a catheter with an extremely low profile and good flexibility at the distal end thereof. Thus, because the collapsed balloons are not filled with the catheter shaft 50, they can collapse to the fullest possible degree.

The first balloon 42 is at least partially inside the second balloon 62. The lengths of the respective balloons are a matter of choice. Thus, if desired, the second balloon 62 may be as long as or longer than the first balloon 42, and may extend substantially to the distal end 74 of the first balloon 42. However, as shown in FIG. 20, it is preferred that the first balloon 42 extend distally from the distal end 76 of the second balloon 62 for at least 15% of the length of the first balloon 42, and preferably for at least about 30% or 40% of the length of the first balloon 42. The first balloon 42 is substantially coaxial with the catheter shaft 50 (or at least the first lumen 54 thereof), and the second balloon 62 is eccentric with respect to the catheter shaft 50 and the guidewire 94. Moreover, the first balloon 42 and the second balloon 62 are eccentric with respect to each other.

As shown in FIG. 21, a cross section of the catheter shaft proximally of the balloons 42, 62, the first lumen 54 has an outer wall 56. The guidewire 94 extends through the first lumen 54. The second lumen 66 has an outer wall 70 on the same side of the guidewire 94 as the outer wall 56 of the first lumen 54. The outer walls 56, 70 of the first and second lumens 54, 66 converge together and are joined at a common lumen wall 72 running from the balloons 42, 62 to the proximal end 46 of the catheter 40.

FIG. 22 is a cross section through both the first and second balloons 42, 62. In this figure, the outer wall 56 of the first lumen 54 has been expanded to form the wall 52 of the first balloon 42. The common lumen wall 72 has also become part of the wall 52 of the first balloon 42. The outer wall 70 of the second lumen 66 has become the wall 64 of the second balloon 62. The first balloon 42 and the second balloon 62 are joined together at at least one wall-to-wall junction 90. Two wall-to-wall junctions 90 are illustrated in FIG. 2.

In FIG. 23, only the wall 52 of the first balloon 42 remains, with the guidewire 94 extending therethrough.

The catheter of FIG. 24 is similar to the catheter of FIG. 20 in that it is a dual balloon axial torque limacon geometry angioplasty catheter. However, instead of overlapping, the first balloon 42 and the second balloon 62 are arranged on the catheter shaft 50 in tandem relationship That is, the first balloon 42 is located distally of the distal end 76 of the second balloon 62. As in the catheter of FIG. 20, the second balloon 42 and the first balloon 62 are eccentric with relation to each other, the second balloon 62 is eccentric with respect to the catheter shaft 50, and the first balloon 42 is generally coaxial with the guidewire 94, the first lumen 54, and the catheter shaft 50.

In the cross section of FIG. 25, the outer wall 70 of the second lumen 66 has become the wall 64 of the balloon 62, while the unexpanded outer wall 56 of the first lumen 54 is substantially inside the second balloon 62. The wall 64 of the second balloon 62 is joined to the outer wall 56 of the first lumen 54 at the common lumen wall 72. FIG. 26 is identical to FIG. 23 and will not be separately described.

The lengths of the first balloon 42 and the second balloon 62 may be similar, and are preferably in the range of from about 12 mm to about 25 mm for coronary angioplasty. The diameters of the first and second balloons 42, 62 may respectively be about 2.0 mm and about 2.5 mm, although in alternative embodiments, they may be increased or decreased by about 0.5 mm.

A triple balloon axial torque guidewire limacon geometry angioplasty catheter is illustrated in FIG. 7. This embodiment has a first balloon 42 and a second balloon 62 in tandem relationship in much the same manner as described in connection with FIG. 21. However, a third balloon 84 is provided on the opposite side of the catheter shaft 50 from the second balloon 62 in much the same manner as was described in connection with FIG. 15. The proximal ends of the second balloon 62 and the third balloon 84 are located at roughly the same point along the length of the catheter shaft 50; however, the distal end 92 of the third balloon 84 is preferably located proximally of the distal end 76 of the second balloon 62. The wall 64 of the second balloon 62 and the wall 88 of the third balloon 84 are joined together at wall-to-wall junctions 90 running lengthwise for the length of the third balloon 84.

As illustrated in FIG. 29, a cross section taken through the second balloon 62 between the third balloon 84 and the first balloon 42, the wall 64 of the second balloon 62 surrounds the outer wall 56 of the first lumen 54 with the axial torque guidewire 94 running through the first lumen 54. The wall 64 of the second balloon 62 and the outer wall 56 of the first lumen 54 are joined together at a common wall 72.

FIG. 30, a cross section through the first balloon, is the same as FIGS. 26 and 23 and will not be separately explained.

The diameter of the distal first balloon 42 is preferably smaller than the diameter of the second balloon 62, which is in turn preferably smaller than the diameter of the third balloon 84. The first and third balloons 42, 84 may be approximately the same length, in the range of from about 10 mm to about 20 mm, and the second balloon 62 may be longer, in the range of from about 20 mm to about 30 mm. The diameters of the balloons 42, 62, 84 for coronary angioplasty may respectively be 2.0 mm, 2.5 mm and 3.0 mm. These diameters may each be increased or decreased about 0.5 mm in alternative embodiments.

Figure 32:
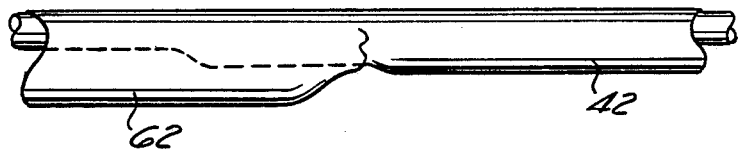
FIG. 32 is a side elevation of a portion of the balloon segment of a catheter of the type illustrated in FIG. 2, showing another embodiment of a joint between two balloons.
Figure 33:
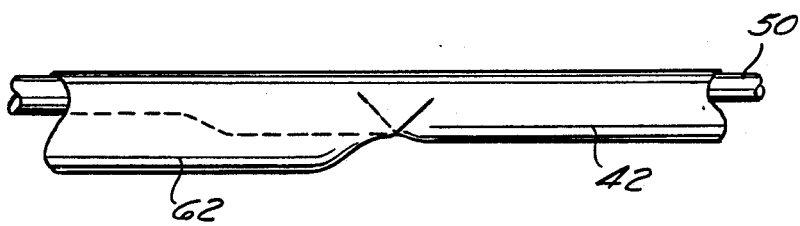
FIG. 33 is a side elevation of a portion of the balloon segment of a catheter of the type illustrated in FIG. 2, showing yet another embodiment of a joint between two balloons.

FIGS. 31-33 illustrate various types of joints that may be formed between the distal end of a balloon and the underlying structure. Although the illustrated joints 79 are between the distal end 76 of a second balloon 62 and an underlying first balloon 42, it should be understood that these joints may represent the joint between any distal end of a balloon and the underlying structure, whether another balloon or the catheter shaft 50.

In FIG. 31, the joint 79 at the distal end 76 of the second balloon 42 is not in a plane perpendicular to the length of the catheter shaft 50, but instead lies in a plane tilted at an acute angle with respect to the length of the catheter shaft 50. This permits smoother and easier passage of the joint 79 through narrowed or tortuous portions or restricted segments of a vessel.

In FIG. 32, the joint 79 describes a wavy or sawtooth line. This type of joint is desirable for the reasons discussed in connection with FIG. 31.

The joint 79 illustrated in FIG. 33 is slanted at an acute angle with respect to the length of the catheter shaft 50, but it is slanted in the direction opposite the direction of the joint in FIG. 31. As shown in phantom in FIG. 33, the joint 79 on the side of the catheter opposite the illustrated side may slant in a direction opposite the direction of the joint 79 on the illustrated side. Alternatively, it may slant in the same direction on both sides.

Although specific embodiments have been described herein, it will be understood that the various balloon structures disclosed may be combined in a large variety of ways, all of which are considered to be within the scope of the present invention. Additional balloons may be added, to provide quadruple or other multiple balloon catheters. Other lumen arrangements may be used. Moreover, the balloon diameters and lengths disclosed in connection with each of the specific illustrated embodiments are preferred coronary angioplasty dimensions. For peripheral and valvular angioplasty, balloon diameters preferably range from about 4 mm to about 10 mm and balloon lengths range from about 30 mm to about 100. Appropriate modifications for such angioplasty are within the scope of the present invention.

III. Limacon Balloon Manufacturing Method

Unlike prior art balloon designs, which contemplate separate extrusion of the catheter shaft and the balloon material, with subsequent attachment of the balloons to the catheter shaft, the present invention permits the balloons to be formed from the catheter shaft material itself, eliminating many of the joints and failure points found in prior art angioplasty catheters and simplifying the fabrication of multiple balloon catheters. Moreover, the fabrication technique is adapted for the manufacture of angioplasty balloon catheters having balloons eccentrically positioned with respect to each other. Thus, if each balloon is considered to have an axis running generally through the middle thereof, the axes of the various balloons will not coincide.

In accordance with the method of the present invention, at least the distal-most end of the catheter is formed from a single, unitary, monolithic piece of polymer material. Preferably, the entire catheter, from proximal end to distal end, is formed from such a single piece of polymer material. The balloons are formed by expanding out the walls of individual lumens running through the catheter shaft at the distal end of the catheter.

After selecting a suitable thermoplastic polymer, the catheter shaft, complete with lumens (or at least the distal-most end of the catheter shaft) is formed by molding or by extrusion. Extrusion processes are preferred, because extrusion is a continuous process and may be used to form long lengths of catheter shaft material which may be cut into the appropriate length for individual catheters. The advantage of molding processes, on the other hand, are that they provide the prospect for combining all sealing or bonding steps into a single molding step, except for possibly the step of sealing a length of catheter shaft material to the molded distal end.

Molded pieces may be directly blown to form balloons. Extruded pieces, on the other hand, require some additional preparation. The extruded piece has a plurality of lumens therethrough having appropriate geometries, e.g., geometries as shown in FIGS. 3, 8, 16 or 21, or variations and adaptations of those geometries suitable for making other balloon configurations falling within the scope of the present invention. In each of the designs, the outer walls of the lumens may be thinner than the common lumen walls to provide for adequate thinning when the balloons are blown therefrom. Moreover, any desired portion of the catheter shaft may be thinned and/or elongated by heating and longitudinally or axially stretching the catheter shaft, either prior to proceeding with the other fabrication steps, or at any desired point in the process. Such stretching, for example, may be used to reduce the diameter of the catheter shaft.

Next, the outer walls of the lumens are removed as appropriate from the point at which the distal end of each balloon is to be located and extending to the distal end of the catheter. In other words, some of the lumens may be shortened by removing the outer wall thereof so the lumen does not extend all the way to the distal end of the catheter. This removal step is preferably accomplished by cutting away the outer lumen wall. With each lumen terminating at the point where the end of the balloon formed from the outer wall of the lumen is to have its distal end, the open lumen ends are sealed to either the underlying catheter shaft or to the underlying lumen wall, as appropriate. In axial torque multiple balloon catheters, the distal end of at least one of the lumens is sealed to the axial torque wire itself either at this point or after blowing the balloons.

In both the extrusion process and the molding process, the outer walls of the lumens adjacent to their sealed, distal ends are then heated to soften the thermoplastic material to the point where it can be blown to form balloons. The balloons may advantageously be blown one at a time inside a die having appropriate dimensions. The dimensions of the finished balloon are determined by the dimensions of the interior of the die. A heated die is preferred. Measures well known in the art to prevent sticking of overlapping balloon layers and sticking of balloon material to the die should be employed. Moreover, while applying pressure to one lumen to blow the outer wall thereof at the distal end thereof into a balloon, collapse of other lumens must be prevented, either by applying a lesser pressure to those lumens or by inserting a solid or particulate filler or a trochar into the lumen. Blowing of innermost balloons first is preferred, with an appropriate adhesion-prevention powder (such as talcum powder), if required, inside lumens overlying the balloon being blown. The overlying balloons are then blown in sequence from innermost to outermost.

In some instances and with some thermoplastic materials, stiffening of the catheter shaft itself may be desirable. This is particularly true with steerable guidewire-type catheters. Such stiffening may be accomplished in any of a number of ways, such as by inserting a stiffening material, solid, tubular, or any other suitable geometry, into one of the lumens or incorporating the stiffening material directly into the catheter shaft. Alternatively, the stiffening material may be bonded to the outside of the catheter shaft or the catheter shaft may be completely surrounded by the stiffening material.

The aforementioned technique, while described in terms of multiple-balloon catheters, may also be used to fabricate steerable guidewire-type single balloon catheters.

IV. Surgical Procedure Utilizing Limacon Balloon Catheters

In connection with the new catheter designs set forth above, a surgical procedure utilizing those balloons to permit multi-vessel coronary or peripheral angioplasty in a greatly reduced time as compared to current techniques has been developed. This new percutaneous transluminal coronary angioplasty (PTCA) technique for multi-vessel disease is explained below in connection with a schematic drawing illustrating particular locations of cardiovascular disease. Of course, it will be understood that the present technique can be utilized, in one form or another, with any of the multiballoon catheter designs disclosed in the present application, and that utilization of the technique is not limited to the particular disease locations exemplified and illustrated in the following discussion and the accompanying figure.

Figure 34:
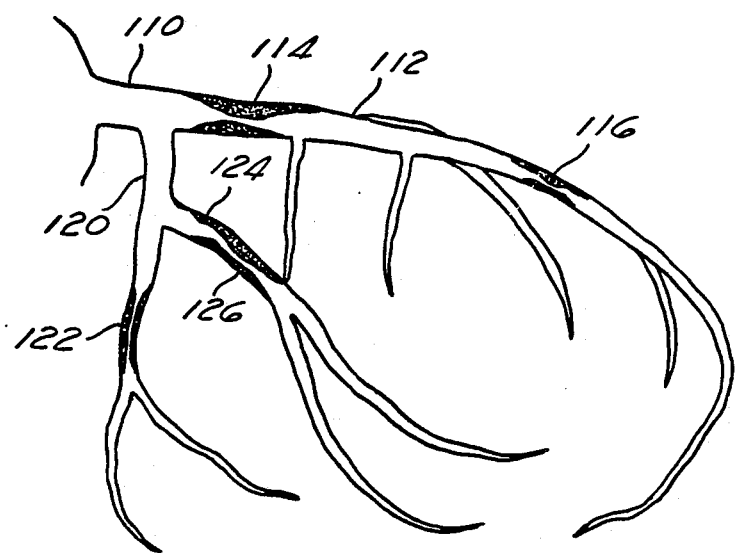
FIG. 34 is a diagram of the left coronary artery system.

A model of the left coronary system having multiple lesions in vessels of various diameter has been adopted for purposes of this description. The diagram used in this description, FIG. 34, represents a hypothetical but not unrealistic case. It should be understood, of course, that the new surgical technique described herein can be used in either the left or the right coronary artery, or in both arteries as a part of the same surgical procedure. What is critical for successful dilation of the lesions in question is that each dilation should be performed with a balloon having a predetermined maximum inflated diameter matching the native diameter of the arterosclerotic vessel.

FIG. 34 is a diagram of the left coronary artery system. The left main artery 110 branches into the left anterior descending (LAD) artery 112, in which two arterosclerotic lesions are illustrated. The first lesion 114 is located in the proximal portion of the LAD, in a vessel having a native diameter of 3.0 mm. The second lesion 116 is located in the distal LAD in a vessel having a native diameter of 2.0 mm. The circumflex artery 120 branches off of the left main artery 110. A third lesion 122 is illustrated in the circumflex artery 120, in a vessel having a native diameter of 2.0 mm. Finally, the obtuse marginal artery 124 (OMA) branches from the circumflex artery 120. A fourth lesion 126 is illustrated in the OMA 124 in a vessel having a native diameter of 2.5 mm.

With currently available PCTA techniques, three separate PCTA catheters would be needed to perform multi-vessel PTCA in this model. One of the catheters required would have a balloon of 3.0 mm, one a balloon of 2.5 mm, and one a balloon of 2.0 mm. With the procedure of the present invention, only one specially designed PCTA catheter is needed As a result, the necessity for catheter exchange is eliminated, and the amount of X-ray exposure, the amount of contrast material injected, and the length of the PCTA procedure are all reduced.

The present invention may be used in the left coronary artery system having the lesions illustrated in FIG. 31 in the following way.

The patient is prepared and a conventional guiding catheter is inserted through the aorta into the left main artery 110. Any suitable triple balloon catheter (or a dual balloon catheter having two partially-overlapping balloons on opposite sides of the catheter shaft) of the type described previously herein is advanced through the guiding catheter and into the LAD 112. The triple balloon catheter is provided with a first balloon having a maximum inflated diameter of 2.0 mm, a second balloon having a maximum inflated diameter of 2.5 mm, and a third balloon (or two combined balloons) having a maximum inflated diameter of 3.0 mm. Of course, all three balloons have been deflated with negative pressure as the catheter is advanced into the first lesion 114 in the LAD 112.

When the 3.0 mm third balloon is properly positioned inside the first lesion 114, as verified by radiography showing the location of the radiopaque marker inside the third balloon, the third balloon is selectively inflated while the other balloons remain collapsed. When proper dilation of the lesion 114 has been achieved, the third balloon is deflated by applying negative pressure to the third lumen. The balloon catheter is then advanced to the next target lesion with all three balloons completely deflated.

The balloon catheter is next advanced distally into the LAD 112 until the 2.0 mm first balloon is positioned inside the second lesion 116. Once the deflated 2.0 mm first balloon is centered in the second lesion 116, the first balloon is inflated to dilate the second lesion 116.

When the lesion 116 has been fully dilated by inflation of the first balloon, negative pressure is applied to fully deflate the first balloon. The catheter is then retracted back to the left main artery 110 and, through use of a steerable guidewire, is then threaded into the obtuse marginal artery 124. Because the fourth lesion 126 in the obtuse marginal artery 124 is in a vessel having a native diameter of 2.5 mm, the second balloon having a maximum inflated diameter of 2.5 mm is positioned inside the fourth lesion 126. The second balloon is then fully inflated to dilate the lesion 126, and is then collapsed as discussed in connection with the previous dilations. The catheter is then withdrawn from the obtuse marginal artery 124 and is inserted into the third lesion 122 in the circumflex artery 120. The third lesion 122, in a vessel having a native diameter of 2.0 mm, is dilated with the first balloon in the same manner as was described in connection with the second lesion 116.

The balloon catheter and the guiding catheter are then withdrawn and the procedure is completed in accordance with standard PCTA techniques.

Although the technique has been described in connection with the left coronary artery system, it is equally applicable in PTCA of the right coronary artery system and in valvular peripheral angioplasty.

Because both the right and the left coronary artery systems are equally susceptible to arterosclerotic disease, often patients will have disease in both coronary arteries at the same time. As long as the lesions are accessible to balloon angioplasty, they may be conveniently and efficiently dilated by the technique described herein using the multi-balloon catheter. The same balloon catheter can be used in both arteries. However, it will typically be necessary to exchange the guiding catheter if the procedure involves a shift from one (left) coronary artery to the other (right) coronary artery. The principle of effective balloon catheter utilization is the same in the two arteries. However, in order to increase efficiency, guiding catheters changed from one artery to the other should be moved in such as way as to avoid a return to a vessel that has previously been entered. This is because each time the procedure is shifted from one artery to the other, it is necessary to exchange the guiding catheter.

The present invention permits full and effective dilation of some lesions that cannot effectively be dilated with a single balloon catheter. In some cases of advanced arterosclerotic disease, a lesion may result in such a reduced diameter that an angioplasty balloon having a maximum inflated diameter the same as the diameter of the native vessel cannot be advanced into the lesion. In this case, a multi-balloon catheter made in accordance with the present invention may be used to good effect. The low profile distal balloon on the catheter, having an inflated diameter less than the native diameter of the vessel, can be advanced into the lesion and inflated to partially dilate the lesion so that the appropriately-sized balloon can be placed inside the lesion and the lesion can be fully dilated. Thus, tight lesions can be predilated with a small balloon first, so that dilation of the lesions can be completed with the larger balloon. It is estimated that 20-25% of the single lesion cases in which balloon angioplasty is now performed currently require a second balloon catheter because the originally-selected balloon catheter is too large to cross the lesion. With the present invention, these constricted single-lesion dilations can now be performed with a single multi-balloon catheter.

Thus, in accordance with one aspect of the procedure of the present invention requires advancing a multi-balloon angioplasty catheter of the type described herein having a plurality of differently-sized balloons into the vessel to be dilated, dilating a first lesion with a balloon having a first diameter, dilating a second lesion with a balloon having a second diameter, and, optionally, dilating a third lesion with a third balloon (or two combined balloons) having a predetermined third diameter appropriate for the third lesion.

In accordance with another aspect of the procedure of the present invention, a single lesion may be dilated with a multi-balloon catheter of the type described herein by advancing a first balloon having a predetermined first diameter into the lesion, and dilating the lesion with the first balloon, and then advancing a second balloon into the lesion, wherein the second balloon has a maximum inflated diameter larger than the maximum inflated diameter of the first balloon, and then dilating the lesion with the second balloon.

What is claimed is:

1. An angioplasty catheter, comprising:
   a catheter shaft having a proximal end and a distal end;
   first and second independently inflatable and independently deflatable angioplasty balloons at the distal end of said catheter, each said balloon having a balloon wall and having a length and a maximum inflated diameter, wherein said balloons and said distal end of said catheter shaft comprise a single, integral, monolithic piece of polymer material and wherein said balloons are eccentrically positioned with respect to each other, wherein said first balloon has a maximum inflated diameter less than that of said second balloon and is at least partially inside said second balloon.

2. The catheter of claim 1, wherein at least 15% but less than 85% of the length of said first balloon is inside said second balloon.

3. An angioplasty catheter, comprising:
   a catheter shaft having a proximal end and a distal end;
   at least two independently inflatable and independently deflatable angioplasty balloons at the distal end of said catheter, each said balloon having a balloon wall and having a length and a maximum inflated diameter, wherein said balloons and said distal end of said catheter shaft comprise a single, monolithic piece of polymer material and wherein said balloons are eccentrically positioned in a radial direction with respect to each other, said catheter shaft includes at least a first lumen and a second lumen extending through said catheter shaft, and said balloons comprise a first balloon and a second balloon, wherein said first lumen terminates inside said first balloon and said second lumen terminates inside said second balloon; and
   an axial torque guidewire extending through said first lumen and out of the distal end of said first balloon and said catheter, wherein the distal end of said first balloon is sealed to said guidewire, wherein the walls of said first balloon have been formed by expanding the walls of said first lumen and wherein said first balloon is substantially coaxial with said first lumen.

4. The catheter of claim 3, wherein the walls of said second balloon have been formed by expanding the walls of said second lumen and wherein said second balloon is eccentric with respect to said second lumen.

5. The catheter of claim 3 or 4, wherein said balloons further comprise a third balloon and wherein said catheter shaft has a third lumen in communication with and terminating inside said third balloon, wherein said third balloon is eccentric with respect to said third lumen.

6. An angioplasty catheter, comprising:
   a catheter shaft having a proximal end, a distal end, and a longitudinal axis extending from said proximal end to said distal end;
   at least two independently inflatable and independently deflatable inelastic angioplasty balloons at the distal end of said catheter, each said balloon having a longitudinal axis and a balloon wall and having a length and a different predetermined maximum inflated working diameter, wherein said balloons and said distal end of said catheter shaft comprise a single, integral monolithic piece of polymer material and wherein said axes of said balloons are eccentrically positioned with respect to each other;
   wherein each balloon has a proximal end and a distal end, and wherein the distal end of one of said balloons is joined to the wall of another of said balloons.

7. A method for making angioplasty balloons, comprising the steps of:
   forming from a single piece of polymer material a length of catheter shaft material having at least a first lumen and a second lumen therein, each lumen having an outer wall, each lumen having a proximal end and a distal end, and each lumen having a common wall where the outer walls of at least two lumens converge;
   closing one end of said first lumen to form a first closed lumen;
   applying pressure to the interior of said first closed lumen and heating the outer wall thereof to expand the outer wall of said first sealed lumen inside a first die to form a first balloon therefrom having dimensions determined by the dimensions of the interior of said die, wherein said common wall of said first lumen comprises one side of said first balloon and wherein said first balloon is joined to said common wall along substantially its entire length.

8. The method of claim 7, further comprising the steps of:
   closing one end of said second lumen to form a second closed lumen;
   applying pressure to the interior of said second closed lumen and heating the outer wall thereof to expand the second closed lumen inside a second die to form a second balloon therefrom having dimensions determined by the dimensions of the interior of said second die, wherein said first balloon and said second balloon each have a longitudinal axis, which axes are eccentric with respect to each other.

9. A method for making angioplasty balloons, comprising the steps of:
   forming from a single piece of polymer material a length of catheter shaft material having at least a first lumen and a second lumen therein, each lumen having an outer wall, each lumen having a proximal end and a distal end, and each lumen having a common wall where the outer walls of at least two lumens converge;
   sealing shut the distal end of said first lumen to form a first closed lumen;
   applying pressure to the interior of said first closed lumen and heating the outer wall thereof to expand the outer wall of said first closed lumen inside a first die to form a first balloon therefrom having dimensions determined by the dimensions of the interior of said die;
   sealing shut the distal end of said second lumen to form a second closed lumen;
   applying pressure to the interior of said second closed lumen and heating the outer wall thereof to expand the second closed lumen inside a second die to form a second balloon therefrom having dimensions determined by the dimensions of the interior of said second die, wherein said first balloon and said second balloon are eccentric with respect to each other, wherein the sealed end of said first lumen is located distally of the sealed end of said second lumen so that the distal end of said first balloon is located distally of the distal end of said second balloon.

10. The method of claim 8, wherein the outer wall of said first lumen is located inside the outer wall of said second lumen.

11. A method for making angioplasty balloons, comprising the steps of:
forming from a single piece of polymer material a length of catheter shaft material having at least a first lumen and a second lumen therein, each lumen having an outer wall, each lumen having a proximal end and a distal end, and each lumen having a common wall where the outer walls of at least two lumens converge;
closing one end of said first lumen to form a first closed lumen;
applying pressure to interior of said first closed lumen and heating the outer wall thereof to expand the outer wall of said first closed lumen inside a first die to form a first balloon therefrom having dimensions determined by the dimensions of the interior of said die;
closing one end of said second lumen to form a second closed lumen;
applying pressure to interior of said second closed lumen and heating the outer wall thereof to expand the second closed lumen inside a second die to form a second balloon therefrom having dimensions determined by the dimensions of the interior of said second die, wherein said first balloon and said second balloon are eccentric with respect to each other, wherein said first balloon and said second balloon are located on opposite sides of said catheter.

12. The method of claim 8, wherein said forming step and said closing step are molding steps.

13. The method of claim 8, wherein said forming step is an extrusion step.

14. A method for making angioplasty balloons, comprising the steps of:
forming from a single piece of polymer material a length of catheter shaft material having at least a first lumen and a second lumen therein, each lumen having an outer wall, each lumen having a proximal end and a distal end, and each lumen having a common wall where the outer walls of at least two lumens converge;
sealing the distal end of said first lumen to form a first sealed lumen;
applying pressure to the interior of said first sealed lumen and heating the outer wall thereof to expand the outer wall of said first sealed lumen inside a first die to form a first balloon therefrom having dimensions determined by the dimensions of the interior of said die;
sealing the distal end of said second lumen to form a second sealed lumen;
applying pressure to the interior of said second sealed lumen and heating the outer wall thereof to expand the second sealed lumen inside a second die to form a second balloon therefrom having dimensions determined by the dimensions of the interior of said second die, wherein said first balloon and said second balloon are eccentric with respect to each other, wherein said forming step is an extrusion step; and
shortening said second lumen prior to sealing the distal end thereof by removing a length of the outer wall of said second lumen at the distalmost end of said second lumen so that the distal end of said second lumen is located proximally of the distal end of said first lumen.

15. The method of claim 14, wherein said sealing step for said second lumen comprises bonding the outer wall of said second lumen at the distal end thereof to the outer wall of said first lumen.

16. The method of claim 14, wherein said sealing step for said second lumen comprises bonding the outer wall of said second lumen at the distal end thereof to said catheter shaft.

17. The method of any one of claims 8–14, wherein said catheter shaft material further has a third lumen therein, further comprising the steps of:
sealing the distal end of said third lumen to form a third sealed lumen;
applying pressure to the proximal end of said third sealed lumen and heating the outer wall thereof to expand the outer wall of said third sealed lumen inside a die to form a third balloon therefrom having dimensions determined by the dimensions of the interior of said die.

18. An angioplasty catheter, comprising:
a catheter shaft having a proximal end, a distal end, and a longitudinal axis extending from said proximal end to said distal end;
at least two independently inflatable and independently deflatable inelastic angioplasty balloons at the distal end of said catheter, each said balloon having a longitudinal axis and a balloon wall and having a length and a different predetermined maximum inflated working diameter, wherein said balloons and said distal end of said catheter shaft comprise a single, integral monolithic piece of polymer material and wherein said axes of said balloons are eccentrically positioned with respect to each other;
wherein the distal end of one of said balloons is bonded to the wall of another of said balloons.

19. An angioplasty catheter, comprising:
a catheter shaft having an axis, a distal end, and a proximal end;
a first independently inflatable angioplasty balloon on a first side of the distal end of said shaft;
a second independently inflatable angioplasty balloon on a second side of the distal end of said shaft, wherein said first balloon and said second balloon are only in part axially coextensive on said catheter shaft;
wherein the distal end of said catheter has a first predetermined diameter when said first balloon is inflated, a different second predetermined diameter when said second balloon is inflated, and a different third predetermined diameter when said first and second balloons are both inflated.

20. An angioplasty catheter, comprising:
a catheter shaft having an axis, a distal end, and a proximal end;
a first independently inflatable angioplasty balloon on a first side of the distal end of said shaft;
a second independently inflatable angioplasty balloon on a second side of the distal end of said shaft, wherein said first balloon and said second balloon are only in part axially coextensive on said catheter shaft;

wherein a first portion of said first balloon is opposite said second balloon on said catheter shaft and a second portion of said first balloon is not, and wherein said first portion has a first predetermined maximum inflated diameter and said second portion has a second, different predetermined maximum inflated diameter.

21. The catheter of claim 20, wherein said second portion of said first balloon is located distally of said first portion.

22. An angioplasty catheter, comprising:
a catheter shaft having an axis, a distal end, and a proximal end;
a first independently inflatable angioplasty balloon coaxially disposed on the distal end of said shaft;
a second independently inflatable angioplasty balloon extending from one side of said first balloon along at least a part of the length of said first balloon so that said first and second balloons are at least in part axially coextensive.

23. The method of claim 8, wherein said second balloon is located distally of said first balloon, wherein said catheter includes an axial torque guidewire extending through said second lumen and said step of closing said second lumen comprising sealing the distal end thereof to said guidewire.

24. The method of claim 15 or 16, wherein said bonding of said outer wall of said second lumen is carried out along a semicircular line.

25. A method for performing balloon angioplasty, comprising the steps of:
positioning the first balloon of the angioplasty catheter of claim 8, 17, or 22 in a first stenosis in a vessel, wherein the maximum inflated diameter of said first balloon is approximately equal to the negative diameter of said vessel at the location of said first stenosis;
inflating said first balloon to dilate said first stenosis;
positioning the second balloon of said catheter in a second stenosis in a vessel, wherein the maximum inflated diameter of said second balloon is approximately equal to the native diameter of said vessel at the location of said second stenosis; and
inflating said second balloon to dilate said second stenosis.

* * * * *